United States Patent [19]

Fields et al.

[11] Patent Number: 5,667,973
[45] Date of Patent: *Sep. 16, 1997

[54] SYSTEM TO DETECT PROTEIN-PROTEIN INTERACTIONS

[75] Inventors: Stanley Fields, East Setauket; Ok-Kyu Song, Stony Brook, both of N.Y.

[73] Assignee: The Research Foundation of State University of New York, Albany, N.Y.

[*] Notice: The term of this patent shall not extend beyond the expiration date of Pat. No. 5,283,173.

[21] Appl. No.: 474,363

[22] Filed: Jun. 7, 1995

Related U.S. Application Data

[63] Continuation of Ser. No. 189,910, Feb. 1, 1994, Pat. No. 5,468,614, which is a continuation of Ser. No. 469,285, Jan. 24, 1990, Pat. No. 5,283,173.

[51] Int. Cl.$^6$ ............................................. C12Q 1/68
[52] U.S. Cl. .................. 435/6; 435/69.1; 435/172.3; 530/350
[58] Field of Search ............... 435/6, 172.3, 69.1, 435/252.3, 801; 436/501, 63, 94, 808; 530/350

[56] References Cited

U.S. PATENT DOCUMENTS 5,283,173  2/1994  Fields et al. ................................. 435/6

OTHER PUBLICATIONS

Chien et al., Proc. Natl. Acad. Sci., 88(21):9578–9582 Nov. 1, 1991.

Stryer, "Biochemistry," published 1981 by W. H. Freeman and Co., pp. 120–123.

*Primary Examiner*—George G. Elliott
*Assistant Examiner*—Scott W. Houtteman
*Attorney, Agent, or Firm*—Hoffmann & Baron

[57] ABSTRACT

A method is provided for detecting the interaction between a first test protein and a second test protein, in vivo, using reconstitution of the activity of a transcriptional activator. This reconstitution makes use of chimeric genes which express hybrid proteins. Two types of hybrid proteins are prepared. The first hybrid contains the DNA-binding domain of a transcriptional activator fused to the first test protein. The second hybrid protein contains a transcriptional activation domain fused to the second test protein. If the two test proteins are able to interact, they bring into close proximity the two domains of the transcriptional activator. This proximity is sufficient to cause transcription, which can be detected by the activity of a marker gene which contains a binding site for the DNA-binding domain.

11 Claims, 2 Drawing Sheets a Native GAL4 b Individual Hybrids With GAL4 Domains c Interaction Between Hybrids Reconstitutes GAL4 Activity

GAL4(1-881)

GAL4(1-147)

GAL4(1-147)-SNF1

SNF4

SNF4-GAL4(768-881)

SYSTEM TO DETECT PROTEIN-PROTEIN INTERACTIONS

This is a continuation of copending application Ser. No. 08/189,910 filed on Feb. 1, 1994, which is a continuation of application Ser. No. 07/469,285 filed on Jan. 24, 1990 and issued on Feb. 1, 1994 as U.S. Pat. No. 5,283,173.

This invention was partially made with Government support under Grant No. DMB 8601949 awarded by the National Science Foundation. The United States Government has certain rights in this invention.

BACKGROUND OF THE INVENTION

1. Field of the Invention

The present invention relates to a method for detecting the interaction of proteins in an in vivo system through the use of fused genes encoding hybrid proteins.

2. Background of the Related Art

A fundamental area of inquiry in biology is the analysis of interactions between proteins. Proteins are complex macromolecules made up of covalently linked chains of amino acids. Each protein assumes a unique three dimensional shape determined principally by its sequence of amino acids. Many proteins consist of smaller units termed domains, which are continuous stretches of amino acids able to fold independently from the rest of the protein. Some of the important forms of proteins are as enzymes, polypeptide hormones, nutrient transporters, structural components of the cell, hemoglobins, antibodies, nucleoproteins, and components of viruses.

Protein-protein interactions enable two or more proteins to associate. A large number of non-covalent bonds form between the proteins when two protein surfaces are precisely matched, and these bonds account for the specificity of recognition. Protein-protein interactions are involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions. For example, some oncogenes encode protein kinases whose enzymetic activity on cellular target proteins leads to the cancerous state. Another example of a protein-protein interaction occurs when a virus infects a cell by recognizing a polypeptide receptor on the surface, and this interaction has been used to design antiviral agents.

Protein-protein interactions have been generally studied in the past using biochemical techniques such as cross-linking, co-immunoprecipitation and co-fractionation by chromatography. A disadvantage of these techniques is that interacting proteins often exist in very low abundance and are, therefore, difficult to detect. Another major disadvantage is that these biochemical techniques involve only the proteins, not the genes encoding them. When an interaction is detected using biochemical methods, the newly identified protein often must be painstakingly isolated and then sequenced to enable the gene encoding it to be obtained. Another disadvantage is that these methods do not immediately provide information about which domains of the interacting proteins are involved in the interaction. Another disadvantage is that small changes in the composition of the interacting proteins cannot be tested easily for their effect on the interaction. A genetic system that is capable of rapidly detecting which proteins interact with a known protein, determining which domains of the proteins interact, and providing the genes for the newly identified interacting proteins has not been available prior to the present invention. Accordingly, to avoid the disadvantages inherent in the biochemical techniques for detecting protein-protein interactions, it would be desirable to have a method for detecting protein-protein interactions using a genetic system. The genetic system described here is based on transcriptional activation. Transcription is the process by which RNA molecules are synthesized using a DNA template. Transcription is regulated by specific sequences in the DNA which indicate when and where RNA synthesis should begin. These sequences correspond to binding sites for proteins, designated transcription factors, which interact with the enzymatic machinery used for the RNA polymerization reaction.

There is evidence that transcription can be activated through the use of two functional domains of a transcription factor: a domain that recognizes and binds to a specific site on the DNA and a domain that is necessary for activation, as reported by Keegan, et el., Science, 231, 699–704 (1986) and Ptashne, Cell, 48, 847–853 (1987). The transcriptional activation domain is thought to function by contacting other proteins involved in transcription. The DNA-binding domain appears to function to position the transcriptional activation domain on the target gene which is to be transcribed. In a few cases now known, these two functions (DNA-binding and activation) reside on separate proteins. One protein binds to the DNA, and the other protein, which activates transcription, binds to the DNA-bound protein, as reported by McKnight et el., Proc. Nat'l. Acad. Sci. USA, 89, 7061–7065 (1987); another example is reviewed by Curran et al., Cell, 55, 395–397 (1988).

Transcriptional activation has been studied using the GAL4 protein of the yeast Saccharomyces cerevisiae. The GAL4 protein is a transcriptional activator required for the expression of genes encoding enzymes of galactose utilization, see Johnston, Microbiol. Rev., 51, 458–476 (1987). It consists of an N-terminal domain which binds to specific DNA sequences designated $UAS_G$, (UAS stands for upstream activation site, G indicates the galactose genes) and a C-terminal domain containing acidic regions, which is necessary to activate transcription, see Keegan et el. (1986), supra., and Ma and Ptashne (1987), supra. As discussed by Keegan et al., the N-terminal domain binds to DNA in a sequence-specific manner but fails to activate transcription. The C-terminal domain cannot activate transcription because it fails to localize to the $UAS_G$, see for example, Brent and Ptashne, Cell, 43, 729–736 (1985). However, Ma and Ptashne have reported (Cell, 51, 113–119 (1987); Cell, 55, 443–446 (1988)) that when both the GAL4 N-terminal domain and C-terminal domain are fused together in the same protein, transcriptional activity is induced. Other proteins also function as transcriptional activators via the same mechanism. For example, the GCN4 protein of Saccharomyces cerevisiae as reported by Hope and Struhl, Cell, 46, 885–894 (1986), the ADRI protein of Saccharomyces cerevisiae as reported by Thukral et al., Molecular and Cellular Biology, 9, 2360–2369, and the human estrogen receptor, as discussed by Kumar et al., Cell, 51, 941–951 (1987) both contain separable domains for DNA binding and for maximal transcriptional activation.

None of the aforementioned articles suggests a genetic system to detect protein-protein interactions in vivo using transcriptional activation as an assay.

Accordingly, it is an object of the present invention to provide such a genetic system and related testing kit for detecting protein-protein interactions.

Another object of this invention is to provide a method and kit by which a multiplicity of proteins, such as those encoded by the entire genome of a cell, can be simultaneously tested for interaction with a known protein.

It is a further object of the present invention to provide a method for detection of protein-protein interactions in which the nucleic acid fragments which encode the interacting proteins are immediately available when a positive test occurs.

Yet another object of the present invention is to provide a method for the identification of new genes.

Another object of the present invention is to provide a method which can be used in the design of peptides to be used therapeutically.

A still further object of the invention is provide a system for testing affinity reagents for protein purification.

SUMMARY OF THE INVENTION

These and other objects are achieved by the present invention which provides a method and a kit for detecting interactions between proteins, in vivo, using reconstitution of the activity of a transcriptional activator. This reconstitution makes use of chimeric genes which express hybrid proteins. Two types of hybrid proteins are prepared. The first hybrid contains the DNA-binding domain of a transcriptional activator fused to the first test protein. The second hybrid protein contains a transcriptional activation domain fused to the second test protein. If the two test proteins are able to interact, they bring into close proximity the two domains of the transcriptional activator. This proximity is sufficient to cause transcription, which can be detected by the activity of a marker gene that contains a binding site for the DNA-binding domain.

One advantage of this method is that a multiplicity of proteins can be simultaneously tested to determine whether any interact with a known protein. For example, a DNA fragment encoding the DNA-binding domain is fused to a DNA fragment encoding the known protein in order to provide one hybrid. This hybrid is introduced into the cells carrying the marker gene. For the second hybrid, a library of plasmids can be constructed which may include, for example, total mammalian complementary DNA (cDNA) fused to the DNA sequence encoding the activation domain. This library is introduced into the cells carrying the first hybrid. If any individual plasmid from the library encodes a protein that is capable of interacting with the known protein, a positive signal may be obtained. In addition, when an interaction between proteins occurs, the gene for the newly identified protein is readily available.

The system can be of value in the identification of new genes. For example, receptors on the cell surface may be identified for known growth factors, toxins, or surface antigens. Proteins that interact with oncogene-encoded products may be discovered, and these proteins can be of therapeutic value.

The system can be used in the design of peptide inhibitors. For example, peptides that interact with enzymes such as proteases or kinases can be identified and then tested in other systems for their ability to inhibit the enzymatic reaction. Peptides that bind to bacterial or viral proteins can be identified and then tested in other systems for their ability to inhibit these bacteria or viruses.

The system can be used to test affinity reagents for protein purification. Peptides or protein domains can be identified that interact with the known protein of interest and these may then be used in a purification protocol for the known protein.

For a better understanding of the present invention, reference is made to the following description, taken together with the accompanying figures, and the scope of which is pointed out in the appended claims.

DETAILED DESCRIPTION OF THE INVENTION

Figure 1A:
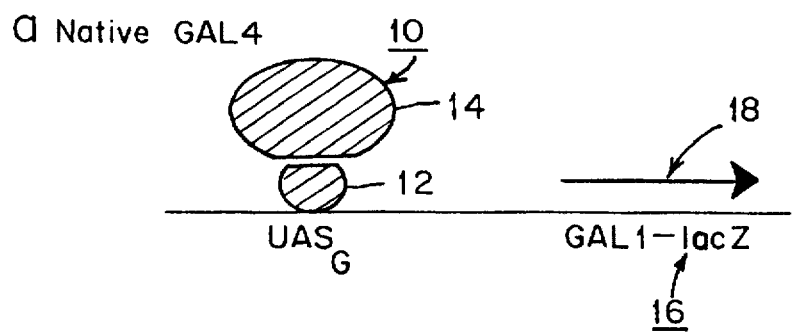
FIGS. 1A–C schematically represents transcriptional activation by reconstitution of GAL4 activity.

A method for detecting the interaction between a first test protein and a second test protein is provided in accordance to the present invention. The method includes providing a host cell, preferably a yeast cell, most preferably *Saccharomyces cerevisiae* or *Schizosaccharomyces pombe*. The host cell contains a detectable gene having a binding site for the DNA-binding domain of the transcriptional activator, such that the detectable gene expresses a detectable protein when the detectable gene is transcriptionally activated. Such activation occurs when the transcriptional activation domain of a transcriptional activator is brought into sufficient proximity to the DNA-binding domain of the transcriptional activator.

A first chimeric gene is provided which is capable of being expressed in the host cell. The first chimeric gene may be present in a chromosome of the host cell. The first chimeric gene comprises a DNA sequence that encodes a first hybrid protein. The first hybrid protein contains a DNA-binding domain that recognizes the binding site on the detectable gene in the host cell. The first hybrid protein also contains a first test protein or protein fragment which is to be tested for interaction with a second test protein or protein fragment.

A second chimeric gene is provided which is capable of being expressed in the host cell. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid. The second chimeric gene contains a DNA sequence that encodes a second hybrid protein. The second hybrid protein contains a transcriptional activation domain. The second hybrid protein also contains a second test protein or a protein fragment which is to be tested for interaction with the first test protein or protein fragment. Preferably, the DNA-binding domain of the first hybrid protein and the transcriptional activation domain of the second hybrid protein are derived from transcriptional activators having separate DNA-binding and transcriptional activation domains. These separate DNA-binding and transcriptional activation domains are also known to be found in the yeast GAL4 protein, and are also known to be found in the yeast GCN4 and ADR1 proteins. Many other proteins involved in transcription also have separable binding and transcriptional activation domains which make them useful for the present invention. In another embodiment, the DNA-binding domain and the transcriptional activation domain may be from different transcriptional activators. The second hybrid protein may be encoded on a library of plasmids that contain genomic, cDNA or synthetically generated DNA sequences fused to the DNA sequence encoding the transcriptional activation domain.

The interaction between the first test protein and the second test protein in the host cell, therefore, causes the transcriptional activation domain to activate transcription of the detectable gene. The method is carried out by introducing the first chimeric gene and the second chimeric gene into the host cell. The host cell is subjected to conditions under which the first hybrid protein and the second hybrid protein are expressed in sufficient quantity for the detectable gene to be activated. The cells are then tested for their expression of the detectable gene to a greater degree than in the absence of an interaction between the first test protein and second test protein.

Thus, interactions between a first test protein and a library of proteins can be tested. For example, the first test protein may be derived from a bacterial protein, a viral protein, an oncogene-encoded protein, a growth factor or an enzyme. The second test protein may be derived from a library of plasmids as described above.

The method of the present invention, as described above, may be practiced using a kit for detecting interaction between a first test protein and a second test protein. The kit includes a container, two vectors, and a host cell. The first vector contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding a first test protein or protein fragment in such a manner that the first test protein is expressed as part of a hybrid protein with the DNA-binding domain. The first vector also includes a means for replicating itself in the host cell and in bacteria. Also included on the first vector is a first marker gene, the expression of which in the host cell permits selection of cells containing the first marker gene from cells that do not contain the first marker gene. Preferably, the first vector is a plasmid.

The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second test protein or protein fragment into the vector, in such a manner that the second test protein is capable of being expressed as part of a hybrid protein with the transcriptional activation domain. Preferably, the DNA-binding domain of the first hybrid protein and the transcriptional activation domain of the second hybrid protein are derived from transcriptional activators having separate DNA-binding and transcriptional activation domains. These separate DNA-binding and transcriptional activation domains are also known to be found in the yeast GAL4 protein, and are also known to be found in the yeast GCN4 and ADR1 proteins. Many other proteins involved in transcription also have separable binding and transcriptional activation domains which make them useful for the present invention. In another embodiment, the DNA binding domain and the transcriptional activation domain may be from different transcriptional activators. The second hybrid protein may be encoded on a library of plasmids that contain genomic, cDNA or synthetically generated DNA sequences fused to the DNA sequence encoding the transcriptional activation domain.

The second vector further includes a means for replicating itself in the host cell and in bacteria. The second vector also includes a second marker gene, the expression of which in the host cell permits selection of cells containing the second marker gene from cells that do not contain the second marker gene.

The kit includes a host cell, preferably a yeast strain of *Saccharomyces cerevisiae* or *Schizosaccharomyces pombe*. The host cell contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene. The host cell, by itself, is incapable of expressing a protein having a function of the first marker gene, the second marker gene, the DNA-binding domain, or the transcriptional activation domain.

Accordingly in using the kit, the interaction of the first test protein and the second test protein in the host cell causes a measurably greater expression of the detectable gene than when the DNA-binding domain and the transcriptional activation domain are present, in the absence of an interaction between the first test protein and the second test protein. The detectable gene may encode an enzyme or other product that can be readily measured. Such measurable activity may include the ability of the cell to grow only when the marker gene is transcribed, or the presence of detectable enzyme activity only when the marker gene is transcribed. Various other markers are well known within the skill of workers in the art.

The cells containing the two hybrid proteins are incubated in an appropriate medium and the culture is monitored for the measurable activity. A positive test for this activity is an indication that the first test protein and the second test protein have interacted. Such interaction brings their respective DNA-binding and transcriptional activation domains into sufficiently close proximity to cause transcription of the marker gene.

In one preferred embodiment, we prepared a system of two hybrid proteins containing domains of a yeast transcriptional activator, the GAL4 protein. A yeast strain is used that carries several genes under the regulation of UAS$_G$ and therefore able to bind the GAL4 DNA-binding domain. One of these genes is GAL1-lacZ, which contains the *E. coli* lacZ gene encoding β-galactosidase. Therefore β-galactosidase activity, detected by liquid assay or by colony color on appropriate media, is a measure of GAL4 function. Growth of the yeast on galactose requires the transcription of genes regulated by GAL4 and is also a measure of GAL4 function. The host yeast strain carries a deletion of the chromosomal GAL4 gene, such that any GAL4 function must be due to that encoded by the introduced plasmids.

The basic strategy of this testing method is shown in FIG. 1. FIG. 1A schematically illustrates the binding of the native GAL4 protein 10 having a DNA-binding domain 12 and a transcriptional activation domain 14. The native GAL4 protein 10, containing both domains 12 and 14, is a potent activator of transcription of the GAL1-lacZ gene 16 when yeast are grown on galactose media. Transcription of the GAL1-lacZ gene 16 is indicated by the arrow 18.

Figure 1B:
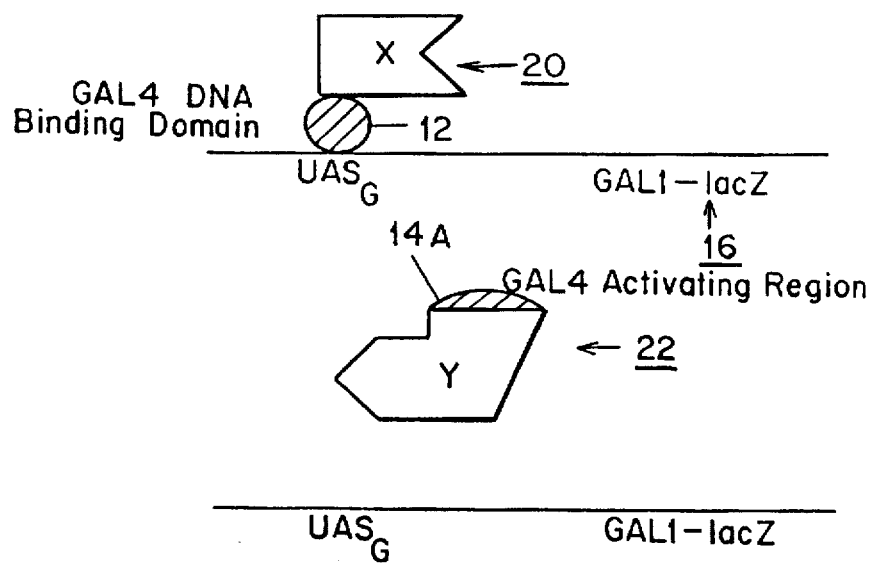
Figure 1C:
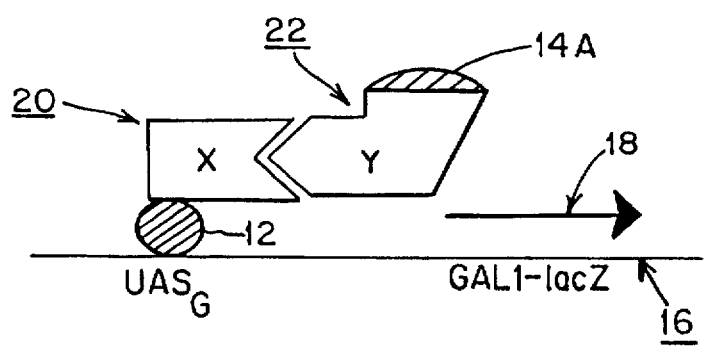

FIG. 1B schematically illustrates two hybrid proteins, 20 and 22. The first hybrid protein 20 contains one of the interacting proteins X and the GAL4 DNA-binding domain 12. The second hybrid protein 22 contains a second interacting protein Y and a portion of the GAL4 activation domain 14A. Neither of these hybrid proteins 20 or 22, alone, is able to activate transcription. The interaction of proteins X and Y, as illustrated in FIG. 1C, allows the portion of the GAL4 activation domain 14A to be brought into sufficient proximity to the DNA-binding domain 12 of GAL4, allowing transcription 18 of GAL1-lacZ gene 16 to occur. Transcriptional activation can be determined by measuring β-galactosidase activity when the yeast are grown on galactose containing media.

The system is dependent on a number of conditions to properly carry out the method of this invention. The first interacting protein X must not, itself, carry an activation domain for the marker. Otherwise the activation domain would allow transcription of the marker gene as soon as the vector encoding only the GAL4 DNA-binding domain fused to the first interacting protein X is introduced. The interaction between the first test protein X and the second test protein Y must be capable of occurring within the yeast nucleus. The GAL4 activation domain portion of the hybrid containing the second test protein Y must be accessible to the transcription machinery of the cell to allow transcription of the marker gene. Should any of these conditions not exist, the system may be modified for use by constructing hybrids that carry only portions of the interacting proteins X and Y and thus meet these conditions.

This system can be used to select genetically for proteins that interact with a known protein, provided the gene encoding the known protein is available. Yeast containing the known protein as a hybrid with the GAL4 DNA-binding domain can be transformed with a clone bank of genomic or cDNA sequences fused to the GAL4 activation domain. The double transformants can be selected for their ability to grow on galactose, or screened for blue color on indicator plates for those transformants able to express the GAL1-lacZ fusion.

Since other eukaryotic cells use a mechanism similar to that of yeast for transcription, other eukaryotic cells such as HeLa cells can be used instead of yeast to test for protein-protein interactions. The reporter gene function can be served by any of a large variety of genes, such as genes encoding drug resistance or metabolic enzymes. The function of GAL4 can be served by any transcriptional activator that has separable domains for DNA-binding and for transcriptional activation. Indeed, any protein, even one that is not a transcriptional activator, that has two separable functions can be used to establish a similar genetic system to detect protein-protein interactions.

Accordingly, the method of the present invention can be applied more generally to any detectable function requiring separable domains of an amino acid sequence which can be reconstituted. This general embodiment of the present invention detects interaction between a first test protein and a second test protein. The method includes providing a host cell which is defective in a detectable function. The detectable function is provided by an amino acid sequence having separable domains. Thus, the amino acid sequence includes a first domain and a second domain which are capable of producing the detectable function when they are in sufficient proximity to each other in the host cell.

A first chimeric gene is provided that is capable of being expressed in the host cell. The first chimeric gene includes a DNA sequence that encodes a first hybrid protein. The first hybrid protein contains the first domain of the amino acid sequence. The first hybrid protein also contains a first test protein or protein fragment which is to be tested for interaction with a second protein or protein fragment.

A second chimeric gene is provided which is capable of being expressed in the host cell. The second chimeric gene contains a DNA sequence that encodes a second hybrid protein. The second hybrid protein contains the second domain of the amino acid sequence. The second hybrid protein also contains a second test protein or protein fragment which is to be tested for interaction with a first test protein or protein fragment.

The interaction between the first test protein and the second test protein in the host cell, causes the function of the amino acid sequence to be reconstituted. The method is thus carried out by introducing the first chimeric gene and the second chimeric gene into the host cell. The host cell is subjected to conditions under which the first hybrid protein and the second hybrid protein are expressed in sufficient quantity for the function of the amino acid sequence to be reconstituted. The cells are then tested to determine whether their expression of the function of the amino acid sequence has been reconstituted to a degree greater than in the absence of the interaction of the test proteins.

This generalized method can be made more specific, for example, as described supra, for the preferred method of the present invention in which the detectable function is transcription of a detectable gene. In this method, the first domain of the amino acid sequence includes a DNA-binding domain that recognizes a binding site on the detectable gene, and the second domain of the amino acid sequence includes a transcriptional activation domain.

In the generalized method, described above, the host cell may be any type of cell, including yeast, bacterial, or mammalian cell. The preferred host cell, however, is a bacterial cell. In carrying out this method, the first test protein may be derived from a bacterial protein, a viral protein, an oncogene-encoded protein, a growth factor or an enzyme. The second hybrid protein may be encoded on a library of plasmids containing DNA inserts that are derived from genomic DNA, cDNA, or synthetically generated DNA sequences fused to the DNA sequence encoding the second amino acid domain.

The following example further illustrates the various features of the invention, and is not intended in any way to limit the scope of the invention which is defined by the appended claims.

EXAMPLE

The method and components of the kit for the present invention were tested using GAL4 as the transcriptional activator and two interacting yeast test proteins, SNF1 and SNF4. We have obtained high transcriptional activity only when both hybrid proteins are present in the yeast cell. The SNF1 protein is a serine-threonine specific protein kinase, as reported by Celenza and Carlson in *Science*, 233, 1175–1180 (1986). The SNF4 protein is physically associated with SNF1 and is required for its maximal activity, see Celenza and Carlson, *Molecular and Cellular Biology*, 9, 5034–5044 (1989) and Celenza, Eng, Carlson, *Molecular and Cellular Biology*, 9, 5045–5054 (1989).

The constructions of the relevant portions of the plasmids used in this example are illustrated in FIG. 2. In FIG. 2, "D" represents the DNA-binding domain of the GAL4 protein; while "A" represents the transcriptional activation domain of the GAL4 protein. FIG. 2A illustrates the entire GAL4 protein of 881 amino acids, designated GAL4 (1–881), based on the gene sequence by Laughon et al., *Molecular and Cellular Biology*, 4, 260–267 (1984). FIG. 2B illustrates the amino terminal 147 amino acids of GAL4, designated GAL4(1–147), which binds to the GAL upstream activation site ($UAS_G$), as described by Keegan et al. (1986), supra. FIG. 2C illustrates the hybrid protein, designated GAL4

Figure 2A:
FIGS. 2A–E schematically represents plasmid constructions used in Example 1.
Figure 2B:
Figure 2C:
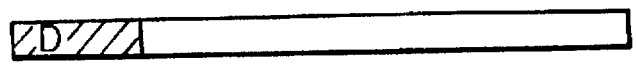
Figure 2D:
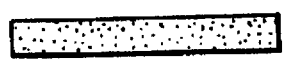
Figure 2E:

(1-147)-SNF1, containing the amino terminal domain of GAL4 fused in frame to the entire coding sequence (633 amino acids) of the SNF1 protein. The sequence of the SNF1 protein is described by Celenza and Carlson in *Science*, 233, 1175–1180 (1986). FIG. 2D illustrates the entire protein designated SNF4, of 322 amino acids, based on the gene sequence by Celenza, Eng, and Carlson (1989) supra. FIG. 2E illustrates a hybrid protein containing all but the last amino acid of SNF4 fused in frame to a GAL4 activation domain, designated SNF4-GAL4(768–881). This GAL4 activation domain is sufficient when fused to the GAL4 DNA-binding domain to induce substantial transcriptional activity of the GAL4 gene, see Ma and Ptashne, *Cell* 48, 847–853 (1987).

The DNA sequence GAL4(1–881) was carried on plasmid pCL1; GAL4(1–147) was carried on plasmid pMA424; GAL4(1–147)-SNF1 was carried on plasmid pEE5; SNF4 was carried on plasmid pFF1; and SNF4-GAL4(768–881) was carried on plasmid pNI12.

These plasmids were introduced into yeast strain GGY1::171 which is deleted for both GAL4 and GAL80, a negative regulator of GAL4, and which also contains a GAL1-lacZ fusion gene, as described by Gill and Ptashne, in *Cell*, 51, 121–126 (1987). Thus β-galactosidase activity is a measure of GAL4 function derived from the plasmid-borne GAL4 constructs. The strain also contains mutations of the HIS3 and LEU2 genes, which are the selectable genes on plasmids containing the DNA-binding and activation domains, respectively.

Transformants were grown in media which can induce transcription from UAS$_G$. The media contained 2% galactose, 2% ethanol, 2% glycerol, and did not contain either leucine or histidine, or both, as appropriate in order to maintain the plasmids.

The results of this experiment are shown in Table 1.

TABLE 1

TRANSCRIPTIONAL ACTIVATION PRODUCED BY HYBRID GAL4 PROTEINS

| Plasmid | β-galactosidase activity |
| --- | --- |
| 1. None | <1 |
| 2. GAL4(1-881) | 4000 |
| 3. GAL4(1-147) | <1 |
| 4. GAL4(1-147)-SNF1 | <1 |
| 5. SNF4 | <1 |
| 6. SNF4-GAL4(768-881) | <1 |
| 7. GAL4(1-147)-SNF1; SNF4-GAL4(768-881) | 180 |
| 8. GAL4(1-147)-SNF1; SNF4 | 7 |
| 9. GAL4(1-147); SNF4-GAL4(768-881) | <1 |

As can be seen in Table 1, in the absence of a plasmid containing GAL4 (line 1), β-galactosidase activity was not detected. By contrast, in the presence of the native GAL4 protein (line 2), 4000 units of β-galactosidase activity were detected. The use of the DNA-binding domain GAL4 (1–147), alone, did not activate transcription and therefore β-galactosidase activity was not detected (line 3). In addition, the use of a plasmid encoding the GAL4(1–147)-SNF1 hybrid protein did not result in β-galactosidase activity (line 4), indicating that the SNF1 protein domain does not function as a transcriptional activation domain.

In addition, introduction of a plasmid encoding either the intact SNF4 protein (line 5), or the SNF4-GAL4(768–881) hybrid protein (line 6), also failed to activate transcription. When plasmids encoding both GAL4(1–147)-SNF1 and SNF4-GAL4(768–881) were introduced, however, 180 units of β-galactosidase activity were detected (line 7). This level of β-galactosidase activity represented an induction of several hundred-fold over the background level of the single hybrids. Although the activity produced by introduction of the two hybrids is only 4.5% of that produced by the native GAL4 protein expressed from the strong ADH1 promoter, it was sufficient to produce a dark blue colony on plates containing the indicator X-gal. X-gal is an abbreviation for 5-bromo-4-chloro-3-indolyl-β-D-galactopyranoside. Accordingly, the yeast cells containing the interacting hybrid proteins which produced blue colonies were easily differentiated from a background of white cells containing only a single hybrid and not expressing β-galactosidase activity.

We have also shown that the induction of transcription and accordingly of β-galactosidase activity produced by the two hybrids is not simply due to the SNF4 protein complexing with the GAL4(1–147)-SNF1 hybrid and converting the GAL4(1–147)-SNF1 hybrid to a transcriptional activator. Thus, introduction of a plasmid encoding the intact SNF4 protein into cells carrying the GAL4(1–147)-SNF1 hybrid was not sufficient for the production of high β-galactosidase activity, although a low level of activity was observed (line 8). In addition, the induction of transcription is not due to the GAL4 activating region interacting with the GAL4 DNA-binding region without the requirement of SNF1–SNF4 interaction (line 9).

The plasmids used in this example were constructed as follows:

pCL1 which contains GAL4(1–881) was constructed by using the BamHI fragment of pLKC15, described by Ma and Ptashne, *Cell*, 48, 847–853 (1987) and Silver et al., in *Proc. Nat'l. Acad. Sci. USA*, 81, 5951–5955 (1984), which contains the P$_{ADH1}$-GAL4 gene. This fragment was inserted into a YCp50 derivative in which the LEU2 gene replaces the URA3 gene.

pMA424 containing the GAL4(1–147) genome was constructed as described by Ma and Ptashne, *Cell*, 51, 113–119 (1987).

pEE5 containing the GAL4(1–147)-SNF1 hybrid is derived from pMA424 and pCC107 of Celenza. pCC107 contains the SNF1 gene in pUC18 and is similar to plasmids described by Celenza and Carlson, *Molecular and Cell Biology*, 9, 5034–5044 (1989). A PstI site, 12 base-pairs upstream of the codon for the initiator methionine of SNF1, was converted to a BamHI site. Then the BamHI fragment containing the SNF1 gene was inserted into the BamHI site pMA424.

pFF1 containing the SNF4 gene was constructed by inserting the HindIII fragment of pFE27-2, as described by Celenza et al., *Molecular and Cell Biology*, 9, 5045–5054 (1989), which contains SNF4 gene, into the multi-copy yeast plasmid YEp13, described in Broach et al. *Gene*, 8, 1221–133 (1979).

pNI12 containing the SNF4-GAL4(768–881) hybrid gene was constructed from a pUC18 clone containing the GAL4 gene and ADH1 terminator (derived from pLKC15) from the NarI site at amino acid 767 of GAL4 to the 3' BamHI site. The NarI site was converted to the KpnI site, and the resulting KpnI fragment was ligated to pSL321, described by Celenza et al., *Molecular and Cell Biology*, 9, 5045–5054 (1989), at a KpnI site, 6 base-pairs downstream of the penultimate amino acid of the SNF4 gene. Then, a HindIII fragment containing the SNF4 promoter and gene fused to the GAL4 (768–881) region was inserted into the plasmid YEp13.

While there have been described what are presently believed to be the preferred embodiments of the invention, those skilled in the art will realize that other changes and modifications may be made thereto without departing from the spirit of the invention, and we intend to claim all such changes and modifications as falling within the true scope of the invention.

We claim:

1. A method for detecting an interaction between a first test protein and a second test protein, the method comprising:

(a) providing a host cell containing a detectable gene wherein the detectable gene expresses a detectable protein when the detectable gene is activated by an amino acid sequence including a transcriptional activation domain when the transcriptional activation domain is in sufficient proximity to the detectable gene;

(b) providing a first chimeric gene that is capable of being expressed in the host cell, the first chimeric gene comprising a DNA sequence that encodes a first hybrid protein, the first hybrid protein comprising:

(i) a DNA-binding domain that recognizes a binding site on the detectable gene in the host cell; and (ii) a first test protein or fragment thereof that is to be tested for interaction with at least one second test protein or fragment thereof;

(c) providing a second chimeric gene that is capable of being expressed in the host cell, the second chimeric gene comprising a DNA sequence that encodes a second hybrid protein, the second hybrid protein comprising:

(i) the transcriptional activation domain; and (ii) a second test protein or fragment thereof that is to be tested for interaction with the first test protein or fragment thereof;

wherein interaction between the first test protein and the second test protein in the host cell causes the transcriptional activation domain to activate transcription of the detectable gene;

(d) introducing the first chimeric gene and the second chimeric gene into the host cell;

(e) subjecting the host cell to conditions under which the first hybrid protein and the second hybrid protein are expressed in sufficient quantity for the detectable gene to be activated; and (f) determining whether the detectable gene has been expressed to a degree greater than expression in the absence of an interaction between the first test protein and the second test protein.

2. The method according to claim 1, wherein the DNA-binding domain and transcriptional activation domain are derived from transcriptional activators having separable DNA-binding and transcriptional activation domains.

3. The method according to claim 2, wherein the DNA binding domain and the transcriptional activation domain are selected from the group consisting of transcriptional activators GAL4, GCN4 and ADR1.

4. The method according to claim 1, wherein the first hybrid protein or the second hybrid protein is encoded on a library of plasmids containing DNA inserts, derived from the group consisting of genomic DNA, cDNA and synthetically generated DNA.

5. The method according to claim 1, wherein the first test protein is derived from the group consisting of bacterial protein, viral protein, oncogene-encoded protein, growth factor and enzyme.

6. The method according to claim 1, wherein the host cell comprises a yeast cell.

7. The method according to claim 6, wherein the yeast cell is selected from the group consisting of *Saccharomyces cerevisiae* and *Schizosaccharomyces pombe*.

8. The method according to claim 1, wherein the chimeric genes are introduced into the host cell in the form of plasmids.

9. The method according to claim 1, wherein the first chimeric gene is integrated into the chromosomes of the host cell.

10. The method according to claim 1, wherein the first chimeric gene is integrated into the chromosomes of the host cell and the second chimeric gene is integrated into the host cell as part of a plasmid.

11. The method according to claim 1, wherein the DNA-binding domain and the transcriptional activation domain are from different transcriptional activators.

* * * * *

UNITED STATES PATENT AND TRADEMARK OFFICE
CERTIFICATE OF CORRECTION

PATENT NO. : 5,667,973
DATED : Sep. 16, 1997
INVENTOR(S): Stanley Fields and Ok-Kyu Song It is certified that error appears in the above-identified patent and that said Letters Patent are hereby corrected as shown below:

Column 2, Line 20, delete "et el." and replace with --et al.--
Column 2, Line 21, before the words "and Plashne" insert --and Ma--
Column 2, Lines 30 and 34, delete "et el." and insert --et al.--
Column 2, Line 56, delete "ADRI" and insert --ADR1--
Column 3, Line 54, delete "enzymetic" and insert --enzymatic--

Signed and Sealed this

Nineteenth Day of May, 1998

Attest:

BRUCE LEHMAN

*Attesting Officer*  *Commissioner of Patents and Trademarks*